United States Patent
Katayama et al.

(10) Patent No.: US 9,119,861 B2
(45) Date of Patent: Sep. 1, 2015

(54) PIROXICAM-CONTAINING TRANSDERMALLY ABSORBABLE PREPARATION

(75) Inventors: Akiko Katayama, Higashikagawa (JP); Katsuyuki Inoo, Higashikagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 0 days.

(21) Appl. No.: 13/516,014

(22) PCT Filed: Dec. 14, 2010

(86) PCT No.: PCT/JP2010/072452
§ 371 (c)(1),
(2), (4) Date: Aug. 20, 2012

(87) PCT Pub. No.: WO2011/074565
PCT Pub. Date: Jun. 23, 2011

(65) Prior Publication Data
US 2012/0309749 A1    Dec. 6, 2012

(30) Foreign Application Priority Data
Dec. 15, 2009  (JP) ................................ 2009-284324

(51) Int. Cl.
*A61K 31/5415* (2006.01)
*A61P 29/00* (2006.01)
*A61K 31/245* (2006.01)
*A61K 9/70* (2006.01)

(52) U.S. Cl.
CPC ........... *A61K 31/5415* (2013.01); *A61K 9/7053* (2013.01); *A61K 31/245* (2013.01)

(58) Field of Classification Search
CPC  A61K 31/5415; A61K 31/245; A61K 9/7053
See application file for complete search history.

(56) References Cited

U.S. PATENT DOCUMENTS

2004/0208914 A1 * 10/2004 Richlin et al. ................ 424/448
2005/0129748 A1 *  6/2005 Takada et al. ................ 424/449
2005/0260186 A1 * 11/2005 Bookbinder et al. ...... 424/94.61

FOREIGN PATENT DOCUMENTS

| JP | 2002-128699 | 5/2002 |
| JP | 2004-123632 | 4/2004 |
| WO | WO 2009/154148 A1 | 12/2009 |

OTHER PUBLICATIONS

International Search Report of PCT/JP2010/072452.

* cited by examiner

*Primary Examiner* — Johann R Richter
*Assistant Examiner* — Katherine Peebles
(74) *Attorney, Agent, or Firm* — Crowell & Moring LLP

(57) ABSTRACT

An adhesive patch is provided in which piroxicam is formulated as a non-steroidal anti-inflammatory analgesic. In particular, provided is a piroxicam-containing transdermally absorbable adhesive patch in which an absorption promoter to piroxicam is formulated to achieve high anti-inflammatory and analgesic effects without inhibiting releasing of these drugs. The piroxicam-containing transdermally absorbable adhesive patch contains piroxicam as a medicinal component and oxybuprocaine or a pharmaceutically acceptable salt thereof as an absorption promoter. In the piroxicam-containing transdermally absorbable adhesive patch, the content of piroxicam is from 0.1% to 5% by weight to the total weight of a drug-containing plaster and the content of oxybuprocaine or the pharmaceutically acceptable salt thereof is from 1% to 30% by weight to the total weight of the drug-containing plaster.

5 Claims, 7 Drawing Sheets

PIROXICAM-CONTAINING TRANSDERMALLY ABSORBABLE PREPARATION

TECHNICAL FIELD

The present invention relates to a transdermally absorbable preparation, and more particularly, to an adhesive patch containing piroxicam, a non-steroidal anti-inflammatory analgesic, as a medicinal component and oxybuprocaine or a pharmaceutically acceptable salt thereof being a local anesthetic and as an absorption promoter to piroxicam.

BACKGROUND ART

A variety of adhesive patches of the transdermally absorbable preparations formulated with various local anesthetics as transdermal absorption promoters for a non-steroidal anti-inflammatory analgesic have been developed and studied for many years (Patent Documents 1 to 9).

This is based on the idea that release of the absorption promoter formulated in the adhesive patch preparation promotes release of the non-steroidal anti-inflammatory analgesic, thereby resulting in an effective transdermally absorbable adhesive patch showing excellent transdermal absorption.

However, many local anesthetics are basic drugs while many non-steroidal anti-inflammatory analgesics are acidic drugs. Therefore, when these drugs were simultaneously formulated in the adhesive patch, these formed salts and inhibited drug releasing of each other thereby to fail to obtain the desired medicinal effect.

PRIOR ART DOCUMENTS

Patent Documents

Patent Document 1: Japanese Patent Application Laid-Open No. 2005-239709
Patent Document 2: Japanese Patent Application Laid-Open No. 2005-145932
Patent Document 3: Japanese Patent Application Laid-Open No. 2005-145931
Patent Document 4: Japanese Patent Application Laid-Open No. 2005-145930
Patent Document 5: Japanese Patent Application Laid-Open No. 2004-285044
Patent Document 6: Japanese Patent Application Laid-Open No. 2004-123632
Patent Document 7: Japanese Patent Application Laid-Open No. 2003-335663
Patent Document 8: Japanese Patent Application Laid-Open No. 2002-128699
Patent Document 9: International Publication No. WO 01/047559

Thus, as for the adhesive patch in which a non-steroidal anti-inflammatory analgesic and a local anesthetic as a transdermal absorption promoter are formulated, it has been desired to develop the transdermally absorbable preparation which achieves high anti-inflammatory and analgesic effects without inhibiting drug releasing of each other.

By the way, among non-steroidal anti-inflammatory analgesics, oxicam-type anti-inflammatory analgesics including piroxicam are widely clinically used due to their excellent effects for chronic rheumatism, osteoarthritis, low back pain, anti-inflammation and analgesia after surgery and so on.

As the external preparations of oxicam-type anti-inflammatory analgesics, a piroxicam ointment has been known so far, but the external adhesive patch containing piroxicam has not been available yet.

Under such circumstances, the present inventors have studied development of the external adhesive patch having excellent transdermal absorption for piroxicam, which is an oxicam-type anti-inflammatory analgesic. In the studies, especially regarding the adhesive patch in which the non-steroidal anti-inflammatory analgesic and the local anesthetic as a transdermal absorption promoter are formulated, the present inventors intensively studied development of the transdermally absorbable preparation which achieves high anti-inflammatory and analgesic effects without significantly inhibiting drug releasing of each other.

As a result, when specific amount of oxybuprocaine, a local anesthetic, was formulated as a transdermal absorption promoter to piroxicam in the external adhesive patch containing piroxicam, it was newly found that extremely good transdermal absorption of piroxicam was obtained by the absorption promoting effect of oxybuprocaine and further such effect was specifically caused by combination of oxybuprocaine and piroxicam, thereby completing the present invention.

SUMMARY OF THE INVENTION

Problems to be Solved by the Invention

Thus, in respect to an adhesive patch in which a local anesthetic and a non-steroidal anti-inflammatory analgesic are formulated, the present invention aims at providing the adhesive patch in which the local anesthetic and the non-steroidal anti-inflammatory analgesic are formulated and high anti-inflammatory and analgesic effects are achieved without inhibiting drug releasing of each other.

Among them, especially regarding the adhesive patch in which piroxicam is formulated as a non-steroidal anti-inflammatory analgesic, the present invention intends to provide a piroxicam-containing transdermally absorbable adhesive patch in which oxybuprocaine is formulated as an absorption promoter to piroxicam and high anti-inflammatory and analgesic effects are achieved without significantly inhibiting drug releasing of each other.

Means for Solving the Problem

A basic aspect of the present invention to solve such problems is a piroxicam-containing transdermally absorbable adhesive patch, which contains piroxicam as a medicinal component and oxybuprocaine or a pharmaceutically acceptable salt thereof as an absorption promoter.

Specifically, the present invention is the piroxicam-containing transdermally absorbable adhesive patch wherein the content of piroxicam is from 0.1% to 5% by weight to the total weight of the drug-containing plaster base material and the content of oxybuprocaine or the pharmaceutically acceptable salt thereof is from 1% to 30% by weight to the total weight of the drug-containing plaster base material.

More specifically, the present invention is the piroxicam-containing transdermally absorbable adhesive patch wherein the formulated ratio of piroxicam to oxybuprocaine or the pharmaceutically acceptable salt thereof is piroxicam:oxybuprocaine<1:2.

Especially, the present invention is the piroxicam-containing transdermally absorbable adhesive patch wherein an adhesive patch base is a rubber polymer and the rubber polymer is a styrene-isoprene-styrene block copolymer.

Effects of the Invention

The present invention provides the piroxicam-containing transdermally absorbable adhesive patch, which contains piroxicam as a medicinal component and oxybuprocaine or the pharmaceutically acceptable salt thereof as an absorption promoter.

Particularly, in the present invention, by formulating a combination of specific amounts of piroxicam and oxybuprocaine as the absorption promoter to piroxicam in the adhesive patch base, high releasing of piroxicam is kept without losing releasing of oxybuprocaine significantly, thereby providing a transdermally absorbable preparation, which achieves excellent anti-inflammatory and analgesic effects.

As found in the results of Test Examples described below, the absorption promoting effect caused by formulating oxybuprocaine is specific only for piroxicam among oxicam-type anti-inflammatory analgesics.

Thus, the present invention has a great medical effect in that the adhesive patch of the transdermally absorbable preparation containing clinically extremely useful piroxicam can be provided.

EMBODIMENTS FOR CARRYING OUT THE INVENTION

Figure 1:
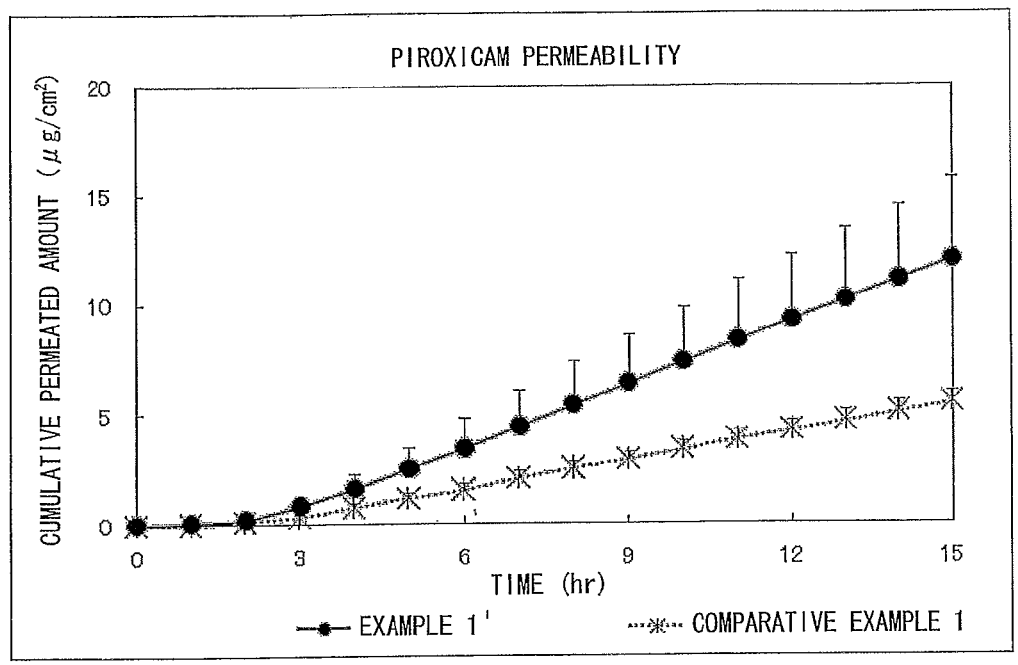
FIG. 1 is a graph showing the result of in vitro rat skin permeability test for piroxicam based on Comparative Study (1)-1.

The present invention is, as described above, a piroxicam-containing transdermally absorbable adhesive patch which contains piroxicam as a medicinal component and oxybuprocaine or a pharmaceutically acceptable salt thereof as an absorption promoter.

The formulated amount of the active component piroxicam in the adhesive patch of the present invention is from 0.1% to 5% by weight, preferably from 0.1% to 3% by weight and particularly preferably from 0.1% to 2% by weight to the total weight of the drug-containing plaster base material.

When the formulated amount of piroxicam is less than 0.1% by weight, the medicinal effect of piroxicam may not be sufficient. Further, more than 5% by weight of piroxicam is not preferable because the absorption promoting effect of oxybuprocaine is decreased.

On the other hand, in the present invention, oxybuprocaine, which is formulated with piroxicam not only shows an analgesic action as a local anesthetic by itself but also serves as the absorption promoter to piroxicam in the present invention.

In this case, the formulated amount of oxybuprocaine is preferably from 1% to 30% by weight and more preferably from 1% to 20% by weight to the total weight of the drug-containing base material.

The formulated amount of less than 1% by weight of oxybuprocaine cannot enhance the skin permeability of piroxicam sufficiently. On the other hand, more than 30% by weight of oxybuprocaine is also not preferable because not only the effect of oxybuprocaine formulated cannot be expected but also irritation to the skin may be caused or the physical properties of the plaster may be lost.

In the present invention, by formulating oxybuprocaine with piroxicam in the adhesive patch base material, the effects such as excellent drug releasing of piroxicam can be obtained without significantly inhibiting drug releasing of oxybuprocaine.

As a result of the studies of the present inventors, it was found that the formulated ratio regarding the formulated amount of piroxicam to oxybuprocaine was preferably piroxicam:oxybuprocaine<1:2. The formulated ratio is more preferably piroxicam:oxybuprocaine<1:10 and particularly preferably piroxicam:oxybuprocaine<1:15.

Even if the formulated ratio of piroxicam to oxybuprocaine is greater than 1:2 (i.e. even if the formulated ratio of piroxicam is greater than the ratio stated above), the releasing of piroxicam tends to be plateau and the release of oxybuprocaine rather can be inhibited.

The plaster composition used in the adhesive patch provided by the present invention can be prepared by mixing piroxicam and oxybuprocaine with an adhesive patch base component.

Such an adhesive patch base component is not particularly limited as long as it can become the base of an adhesive layer which is the plaster composition, and hydrophobic polymers such as a rubber polymer, an acrylic polymer and a silicon polymer are preferably used.

Examples of the rubber polymer may include a styrene-isoprene-styrene block copolymer (hereinafter, referred to as SIS), polyisobutylene (hereinafter, referred to as PIB), a styrene-butadiene-styrene block copolymer (hereinafter, referred to as SBS), a styrene-butadiene rubber (hereinafter, referred to as SBR), an isoprene rubber and the like. Among them, SIS is particularly preferred.

Also, the acrylic polymer is not particularly limited as long as one of (meth)acrylic acid derivatives represented by 2-ethylhexyl acrylate, methyl acrylate, butyl acrylate, hydroxyethyl acrylate, 2-ethylhexyl methacrylate and the like is contained and copolymerized. For example, the adhesives listed in Japanese Pharmaceutical Excipients Directory 2007 (edited by International Pharmaceutical Excipients Council Japan) such as the adhesive of an acrylic polymer which contains an acrylic acid/octyl acrylate copolymer, a 2-ethylhexyl acrylate/vinylpyrrolidone copolymer solution, an acrylate-vinyl acetate copolymer, a 2-ethylhexyl acrylate-2-ethylhexyl methacrylate/dodecyl methacrylate copolymer, a methyl acrylate-2-ethylhexyl acrylate copolymer resin emulsion, an acrylic resin alkanol amine solution and the like, DURO-TAK acrylic adhesive series (produced by National Starch and Chemical Company) and Eudragit series (HIGUCHI Inc.) can be used.

Moreover, specific examples of the silicon polymer may include a silicone rubber such as polyorganosiloxane.

Such hydrophobic polymers may be used in mixture of two or more. The formulated amount of such polymers based on the mass of the total composition is from 5% to 80% by weight, preferably from 10% to 70% by weight and more preferably from 10% to 50% by weight in consideration of the formation of the adhesive layer and sufficient drug permeability.

The adhesive composition in the adhesive patch which is the transdermally absorbable preparation provided by the present invention may contain a plasticizer. Examples of the plasticizer which can be used may include a petroleum-based oil (for example, a paraffin-based process oil such as a liquid paraffin, a naphthene-based process oil, an aromatic process oil and the like), squalane, squalene, a vegetable oil (for example, an olive oil, a camellia oil, a tall oil, a peanut oil, a castor oil and the like), a silicone oil, dibasic acid ester (for example, dibutyl phthalate, dioctyl phthalate and the like), a liquid rubber (for example, polybutene, a liquid isoprene rubber and the like), liquid fatty acid esters (for example, isopropyl myristate, hexyl laurate, diethyl sebacate, diisopropyl sebacate and the like). A liquid paraffin is particularly preferred.

Such components may be used in mixture of two or more. The formulated amount of such plasticizers based on the total composition of the adhesive layer is from 1% to 70% by weight, preferably from 10% to 60% by weight and more preferably from 10% to 50% by weight in total in consideration of the maintaining of enough cohesion as the adhesive patch.

In the adhesive layer of the present invention, it is desirable to formulate a tackifier resin to adjust the adhesion of the preparation. Examples of the tackifier resin which can be used may include rosin derivatives (for example, rosin, rosin glycerin ester, hydrogenated rosin, hydrogenated rosin glycerin ester, rosin pentaerythritol ester and the like), an alicyclic saturated hydrocarbon resin (for example, Alcon P100, Arakawa Chemical Industries Ltd.), an aliphatic hydrocarbon resin (for example, Quinton B170, Nippon Zeon Co., Ltd.), a terpene resin (for example, Clearon P-125, Yasuhara Chemical Co., Ltd.), a maleic acid resin and the like.

The formulated amount of such a tackifier resin based on the total composition of the adhesive composition can be from 5% to 70% by weight, preferably from 5% to 60% by weight and more preferably from 10% to 50% by weight in consideration of enough adhesion as the adhesive preparation and irritation to the skin upon being peeled.

Also, an antioxidant, a filler, a cross-linking agent, a preservative and an ultraviolet absorber can be used if necessary. As the antioxidant, tocopherol and ester derivatives thereof, ascorbic acid, ascorbyl stearate, nordihydroguaiaretic acid, dibutylhydroxy-toluene (hereinafter, referred to as BHT), butylhydroxyanisole and the like are desirable.

As the filler, calcium carbonate, magnesium carbonate, silicate (for example, aluminum silicate, magnesium silicate and the like), silicic acid, barium sulfate, calcium sulfate, calcium zincate, zinc oxide, titanium oxide and the like are desirable.

As the cross-linking agent, a thermosetting resin such as an amino resin, a phenolic resin, an epoxy resin, an alkyd resin and unsaturated polyester; an isocyanate compound; a blocked isocyanate compound; an organic cross-linking agent; and an inorganic cross-linking agent such as a metal and a metal compound are desirable.

As the preservative, paraben such as ethyl parahydroxybenzoate, propyl parahydroxybenzoate and butyl parahydroxybenzoate is desirable.

As the ultraviolet absorber, p-aminobenzoic acid derivatives, anthranilic acid derivatives, salicylic acid derivatives, amino acid compounds, dioxane derivatives, coumarin derivatives, imidazoline derivatives, pyrimidine derivatives and the like are desirable.

Such an antioxidant, a filler, a cross-linking agent, a preservative and an ultraviolet absorber can be formulated in 10% by weight or less, preferably 5% by weight or less and more preferably 2% by weight or less based on the mass of the total composition of the adhesive layer of the preparation.

The adhesive patch, which is the transdermally absorbable preparation of the present invention having the composition described above, can be produced by any methods.

Examples of the methods include generally called a hot melt method and a solvent method. In the hot melt method, the adhesive patch can be obtained by thermally melting the drug-containing base component, coating it on a release film or a support, and laminating the base component to a support or a release film. In the solvent method, the adhesive patch can be obtained by dissolving the drug-containing base component in an organic solvent such as toluene, hexane, ethyl acetate or N-methyl-2-pyrrolidone, spreading and coating it on a release film or a support, removing the solvent by drying, and laminating the base component to a support or a release film.

In the adhesive patch, which is the external transdermal preparation provided by the present invention, the thickness of the adhesive layer is not particularly limited, but generally 500 µm or less and preferably from 20 µm to 300 µm.

As the supporting material of the adhesive patch which is the transdermally absorbable preparation of the present invention, an elastic or a non-elastic support can be used. For example, it is selected from fabrics, nonwoven fabrics, polyurethane, polyester, polyvinyl acetate, polyvinylidene chloride, polyethylene, polyethylene terephthalate (hereinafter, referred to as PET), an aluminum sheet and the like, or the composite material thereof.

The release film is not particularly limited as long as it protects the adhesive layer without the main drug components being decomposed until the adhesive patch, which is the transdermally absorbable preparation, is applied to the skin and it is silicon coated to be easily peeled. Specific examples of the release film include a silicon coated polyethylene film, PET film and polypropylene film.

EXAMPLES

Hereinafter, the present invention will be described more specifically by illustrating Examples, Preparation Examples and Test Examples of the present invention, but the present invention is not limited to these Examples and Preparation Examples and various modifications thereof can be made without departing from the technical idea of the present invention.

Here, in the following description, all of "%" mean "% by weight" unless otherwise specified.

Example 1

0.5% Piroxicam/20% Oxybuprocaine Formulated Preparation

The external adhesive patch in which both piroxicam and oxybuprocaine were formulated was prepared.
(Components)

| | |
|---|---|
| SIS | 25% |
| Liquid paraffin | 11.5% |
| BHT | 1% |
| Hydrogenated rosin glycerin ester | 42% |
| Oxybuprocaine | 20% |
| Piroxicam | 0.5% |
| Total | 100% |

(Process)

Piroxicam was dissolved in advance in N-methyl-2-pyrrolidone and oxybuprocaine was dissolved in toluene. They were mixed with other base components, which were already dissolved in toluene. The mixture was coated on the release film, and subsequently toluene and N-methyl-2-pyrrolidone were removed by drying. The obtained product was laminated with the PET film support to provide a desirable transdermally absorbable preparation (the thickness of the adhesive layer was 100 μm).

Examples 2 to 6

The transdermally absorbable preparations of Examples 2 to 6 of the present invention were obtained in the formulation shown below in Table 1 according to the method described above in Example 1. Here, the formulation of Example 1 is also described in Table 1.

TABLE 1

| | Example (unit: % by weight) | | | | | |
|---|---|---|---|---|---|---|
| Components | 1 | 2 | 3 | 4 | 5 | 6 |
| SIS | 25 | 25 | 25 | 25 | 25 | 25 |
| BHT | 1 | 1 | 1 | 1 | 1 | 1 |
| Hydrogenayef Rosin Glycerin Eeter | 42 | 42 | 42 | 42 | 42 | |
| Alicyclic Saturated Hydrocarbon Resin | | | | | | 42 |
| Liquid Paraffin | 11.5 | 1 | | 29.5 | 17 | 17 |
| Oxybuprocaine | 20 | 30 | 30 | 2 | 10 | 10 |
| Piroxicam | 0.5 | 1 | 2 | 0.5 | 5 | 5 |
| Piroxicam:Oxybuprocaine | 1:40 | 1:30 | 1:15 | 1:4 | 1:2 | 1:2 |

Comparative Examples 1 to 12

The transdermally absorbable preparations of Comparative Examples 1 to 12 were obtained in the formulation shown below in Table 2-(1) to 2-(2) according to the method described above in Example 1.

Table 2-(1)

| | Comparative Example (unit: % by weight) | | | | | |
|---|---|---|---|---|---|---|
| Components | 1 | 2 | 3 | 4 | 5 | 6 |
| SIS | 25 | 25 | 25 | 25 | 25 | 25 |
| BHT | 1 | 1 | 1 | 1 | 1 | 1 |
| Hydrogenated Rosin Glycerin Ester | 42 | 42 | 42 | 42 | | 42 |
| Alicyclic Saturated Hydrocarbon Resin | | | | | 42 | |
| Liquid Paraffin | 31.5 | 31 | 30 | 27 | 27 | 30 |
| Oxybuprocaine | | | | | | 2 |
| Piroxicam | 0.5 | 1 | 2 | 5 | 5 | |
| Meloxicam | | | | | | |

Table 2-(2)

| | Comparative Example (unit: % by weight) | | | | | |
|---|---|---|---|---|---|---|
| Components | 7 | 8 | 9 | 10 | 11 | 12 |
| SIS | 25 | 25 | 25 | 25 | 25 | 25 |
| BHT | 1 | 1 | 1 | 1 | 1 | 1 |
| Hydrogenated Rosin Glycerin Ester | 42 | | 42 | 42 | 42 | 42 |
| Alicyclic Saturated Hydrocarbon Resin | | 42 | | | | |
| Liquid Paraffin | 22 | 22 | 12 | 2 | 11.5 | 31.5 |
| Oxybuprocaine | 10 | 10 | 20 | 30 | 20 | |
| Piroxicam | | | | | | |
| Meloxicam | | | | | 0.5 | 0.5 |

Hereinafter, the tests for Comparative Studies (1) to (2) were carried out by using Examples and Comparative Examples.

[Comparative Study]

(1) A study for releasing of piroxicam and/or oxybuprocaine in comparison of Examples and their corresponding Comparative Examples in regard to the preparations of Examples 1 to 6 in which both piroxicam and oxybuprocaine are formulated in the external adhesive patch of the present invention, the preparations of Comparative Examples 1 to 5 in which only piroxicam is formulated, and the preparations of Comparative Examples 6 to 10 in which only oxybuprocaine is formulated. (The combination of Examples and their corresponding Comparative Examples is shown in Table 3.)

TABLE 3

| Comparative Study Number | Example Number | Comparative Example Number (Only Piroxicam Formulated) | Comparative Example Number (Only Oxybuprocaine Formulated) |
|---|---|---|---|
| (1)-1 | 1 | 1 | 9 |
| (1)-2 | 2 | 2 | 10 |
| (1)-3 | 3 | 3 | 10 |
| (1)-4 | 4 | 1 | 6 |
| (1)-5 | 5 | 4 | 7 |
| (1)-6 | 6 | 5 | 8 |

(2) A study for releasing of meloxicam, which is another oxicam anti-inflammatory analgesic, and oxybuprocaine in comparison of the preparation of Comparative Example 11 in which both meloxicam and oxybuprocaine are formulated, the preparation of Comparative Example 12 in which only meloxicam is formulated and the preparation of Comparative Example 9 in which only oxybuprocaine is formulated.

Test Example 1

Rat Skin Permeability Test

In vitro skin permeability test was carried out with the skin excised from the male rat (Wister strain, 8 week old) for each preparation used in Comparative Study (1)-1, Comparative Study (1)-5, Comparative Study (1)-6 and Comparative Study (2) in Table 3 to study the specificity of the releasing of piroxicam and oxybuprocaine in the external adhesive patch of the present invention in which both piroxicam and oxybuprocaine were formulated.

[Method]

The rat abdominal skin was exfoliated, the dermis side of the skin was directed to a side of a receptor layer, and its inside was filled with phosphate buffered saline. Water kept at 37° C. was circulated in a water jacket. Each test preparation was stamped out in a circle (1.77 $cm^2$) and attached to the excised skin. The receptor solution was sampled over time to measure the permeated amount of each drug (oxybuprocaine, piroxicam, meloxicam) by high performance liquid chromatography.

Test Example 2

Rat Skin Permeability Test

In vitro skin permeability test was carried out with the skin excised from the male hairless rat (HWY strain, 7 week old) for each preparation used in Comparative Study (1)-2, Comparative Study (1)-3, Comparative Study (1)-4 in Table 3 to study the specificity of the releasing of piroxicam and oxybuprocaine in the external adhesive patch of the present invention in which both piroxicam and oxybuprocaine were formulated.

[Method]

The rat abdominal skin was exfoliated, the dermis side of the skin was directed to a side of a receptor layer, and its inside was filled with phosphate buffered saline. Water kept at 37° C. was circulated in a water jacket. Each test preparation was stamped out in a circle (1.77 $cm^2$) and attached to the excised skin. The receptor solution was sampled over time to measure the permeated amount of each drug (oxybuprocaine, piroxicam) by high performance liquid chromatography.

[Result]

The results are shown in FIGS. 1 to 14. The correspondence relation of each figure is shown in Table 4.

TABLE 4

Figure 2:
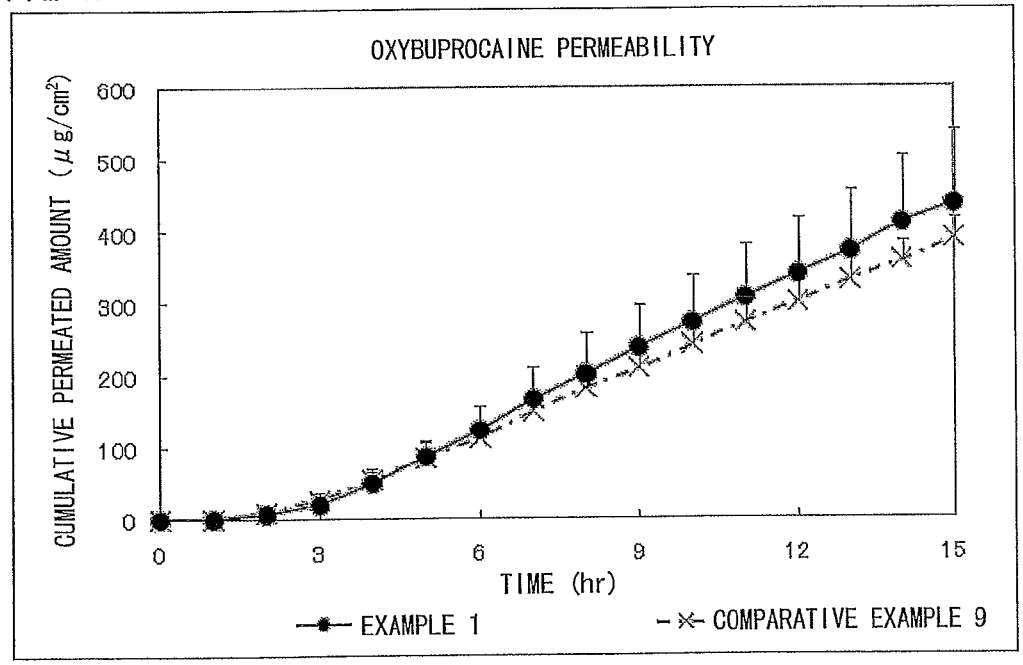
FIG. 2 is a graph showing the result of in vitro rat skin permeability test for oxybuprocaine based on Comparative Study (1)-1.
Figure 3:
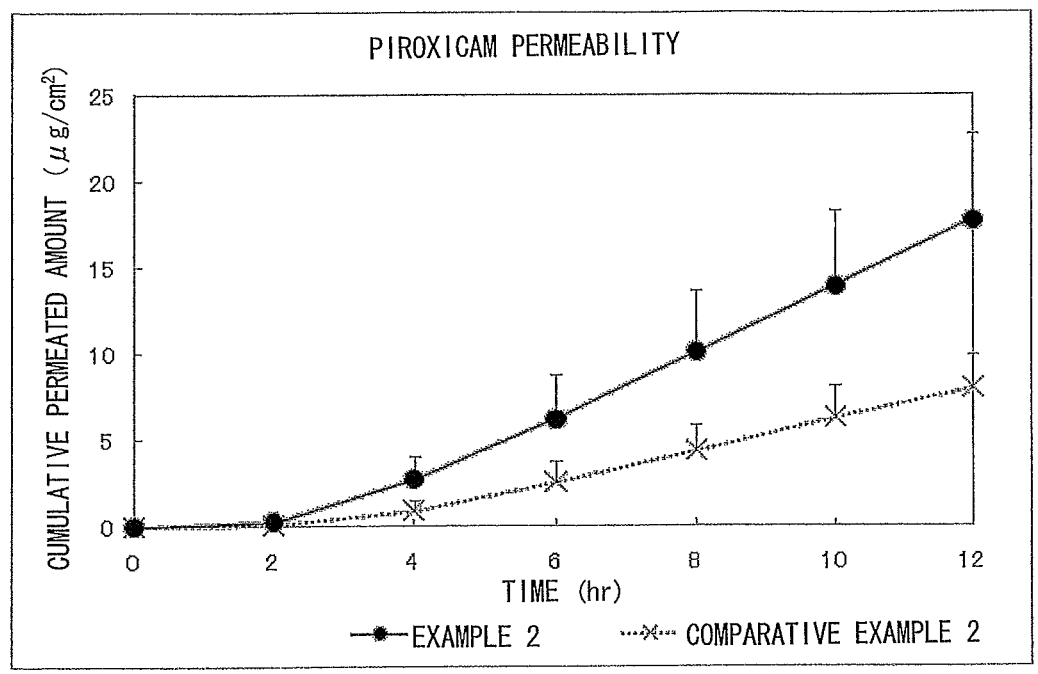
FIG. 3 is a graph showing the result of in vitro rat skin permeability test for piroxicam based on Comparative Study (1)-2.
Figure 4:
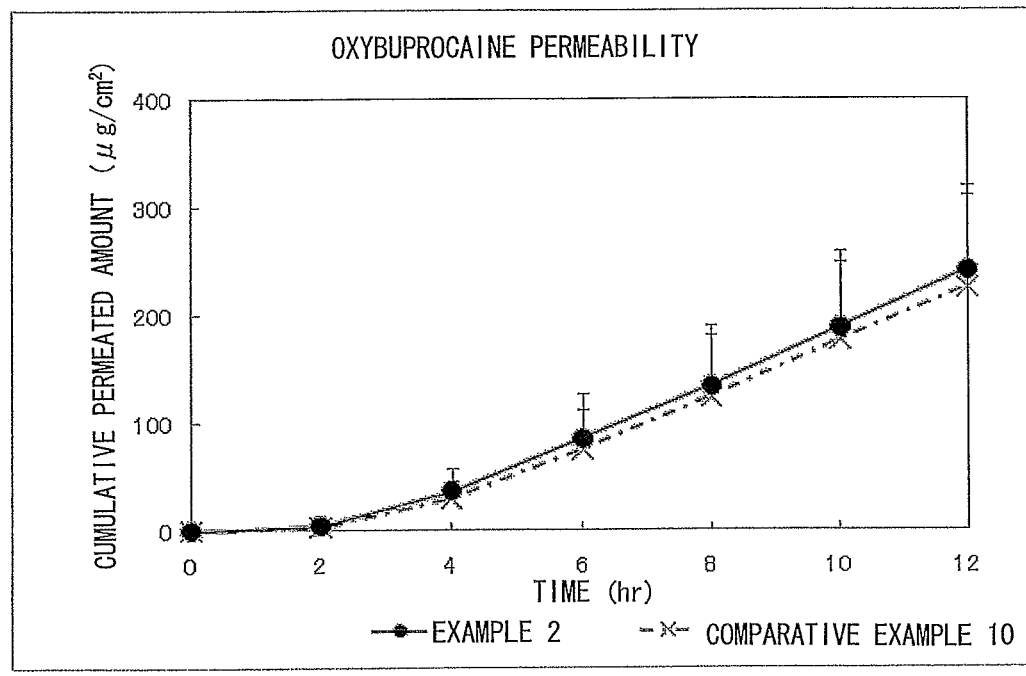
FIG. 4 is a graph showing the result of in vitro rat skin permeability test for oxybuprocaine based on Comparative Study (1)-2.
Figure 5:
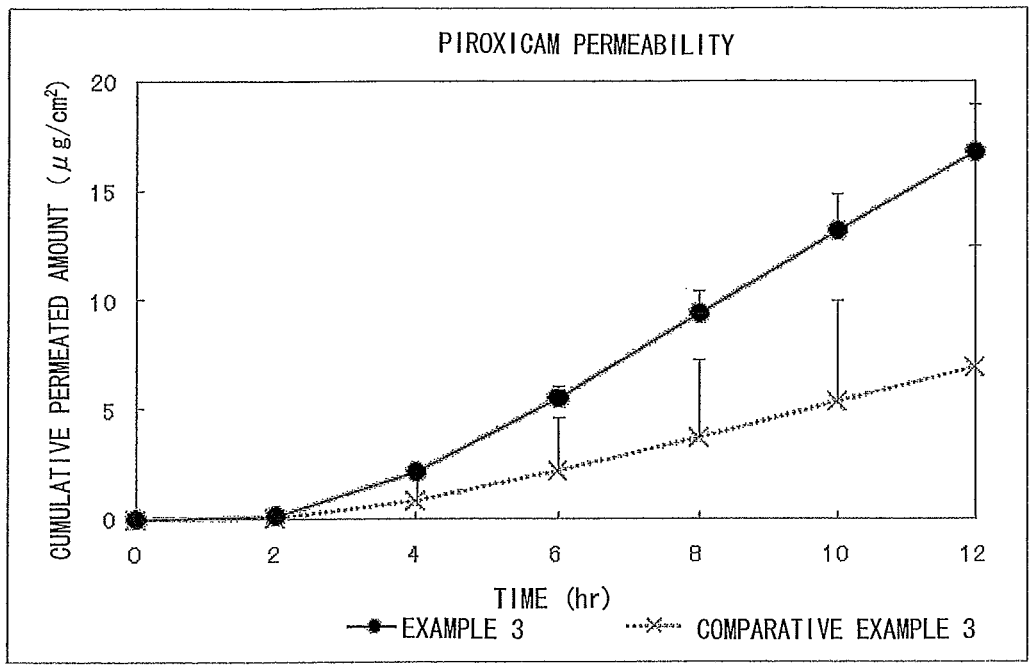
FIG. 5 is a graph showing the result of in vitro rat skin permeability test for piroxicam based on Comparative Study (1)-3.
Figure 6:
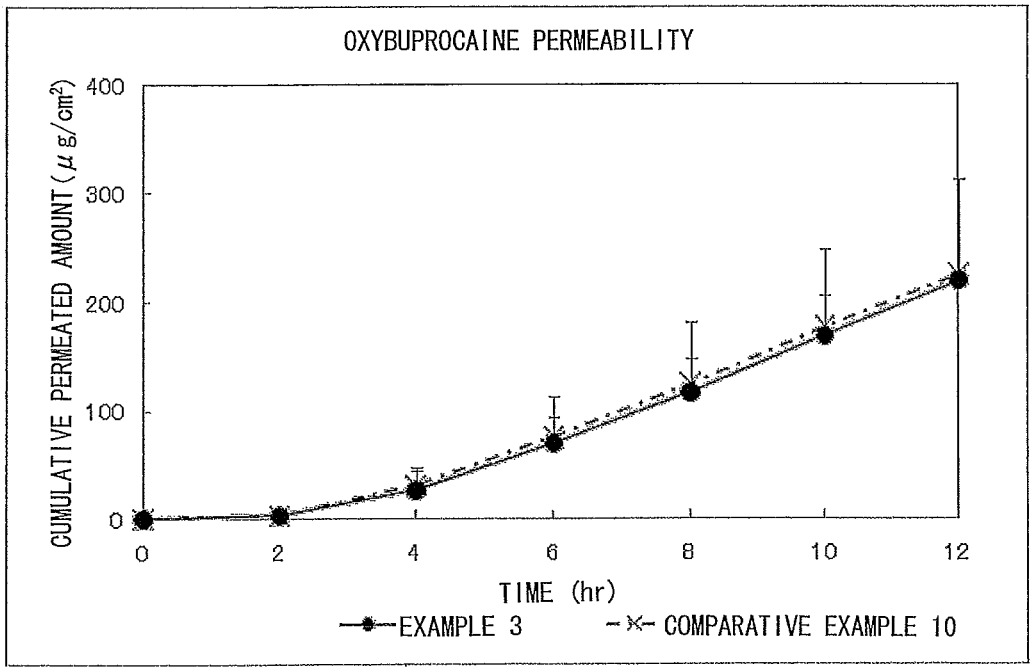
FIG. 6 is a graph showing the result of in vitro rat skin permeability test for oxybuprocaine based on Comparative Study (1)-3.
Figure 7:
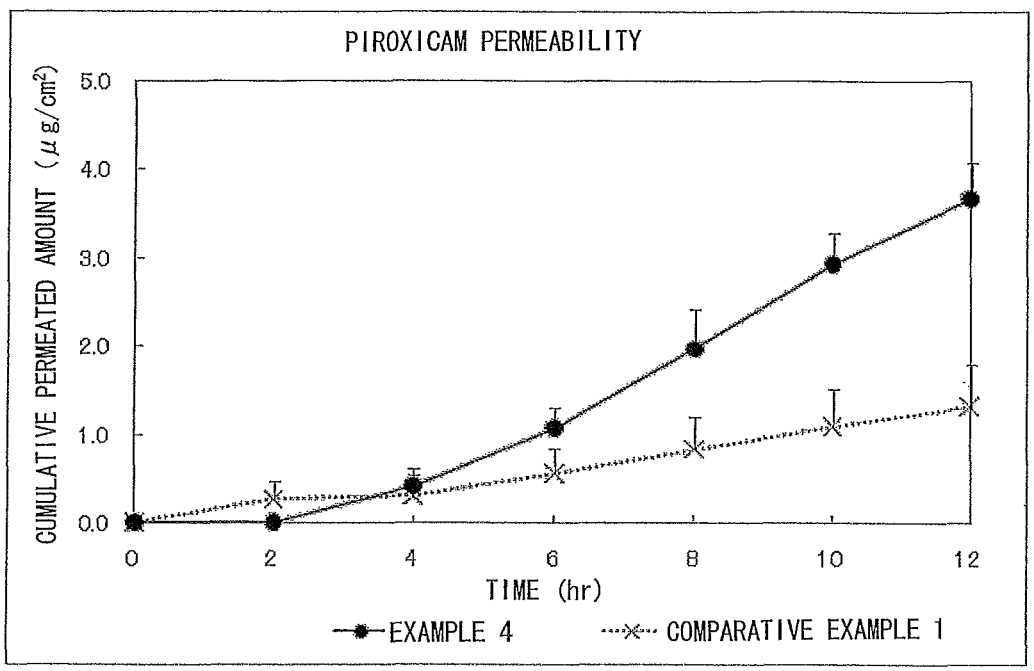
FIG. 7 is a graph showing the result of in vitro rat skin permeability test for piroxicam based on Comparative Study (1)-4.
Figure 8:
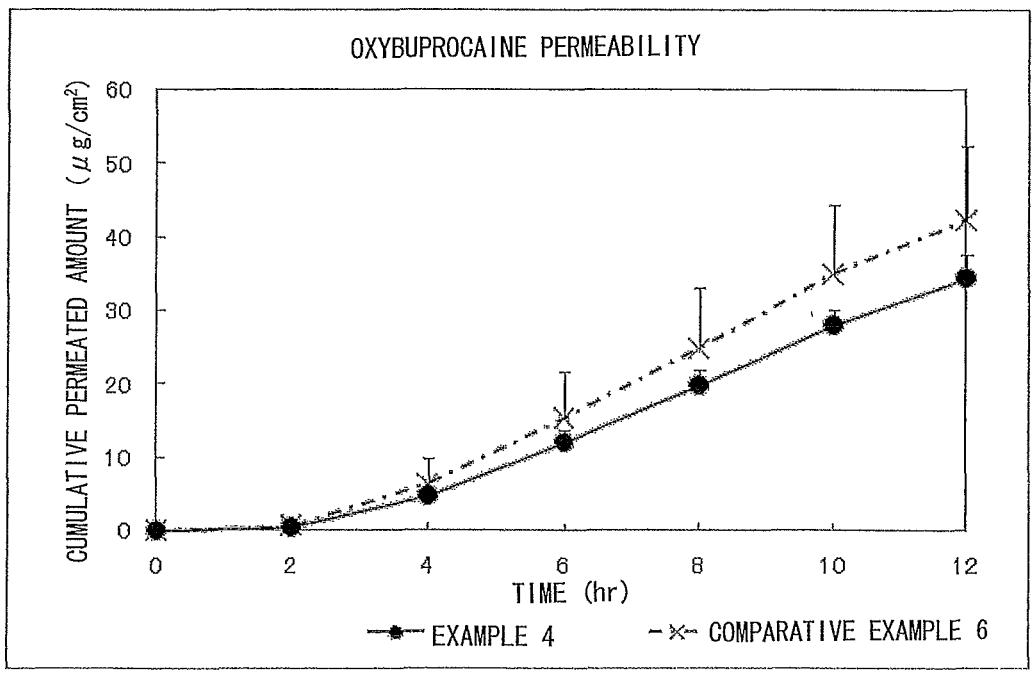
FIG. 8 is a graph showing the result of in vitro rat skin permeability test for oxybuprocaine based on Comparative Study (1)-4.
Figure 9:
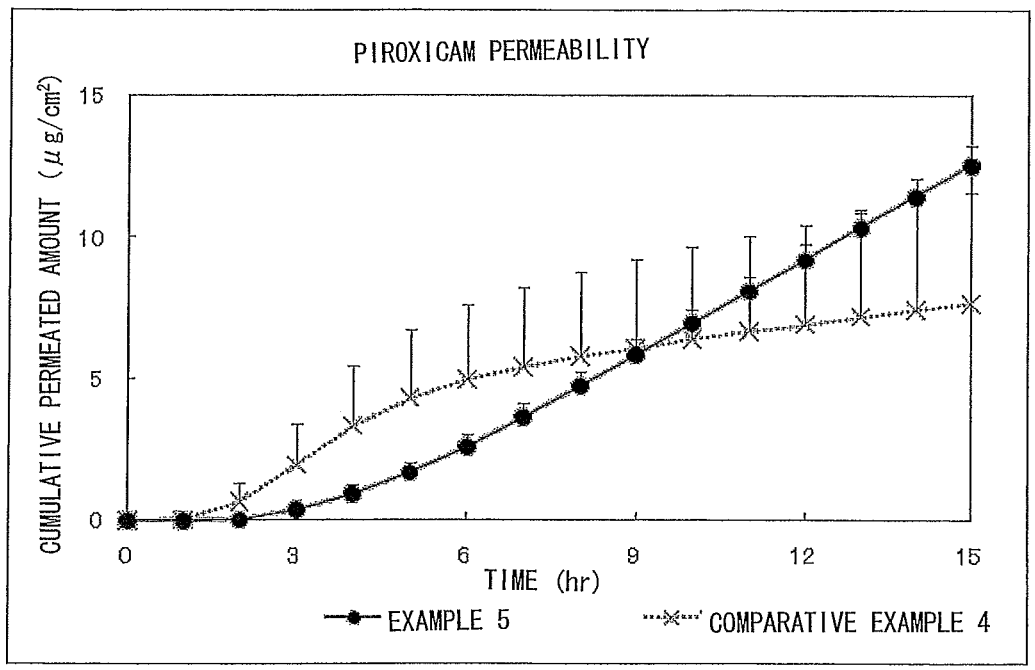
FIG. 9 is a graph showing the result of in vitro rat skin permeability test for piroxicam based on Comparative Study (1)-5.
Figure 10:
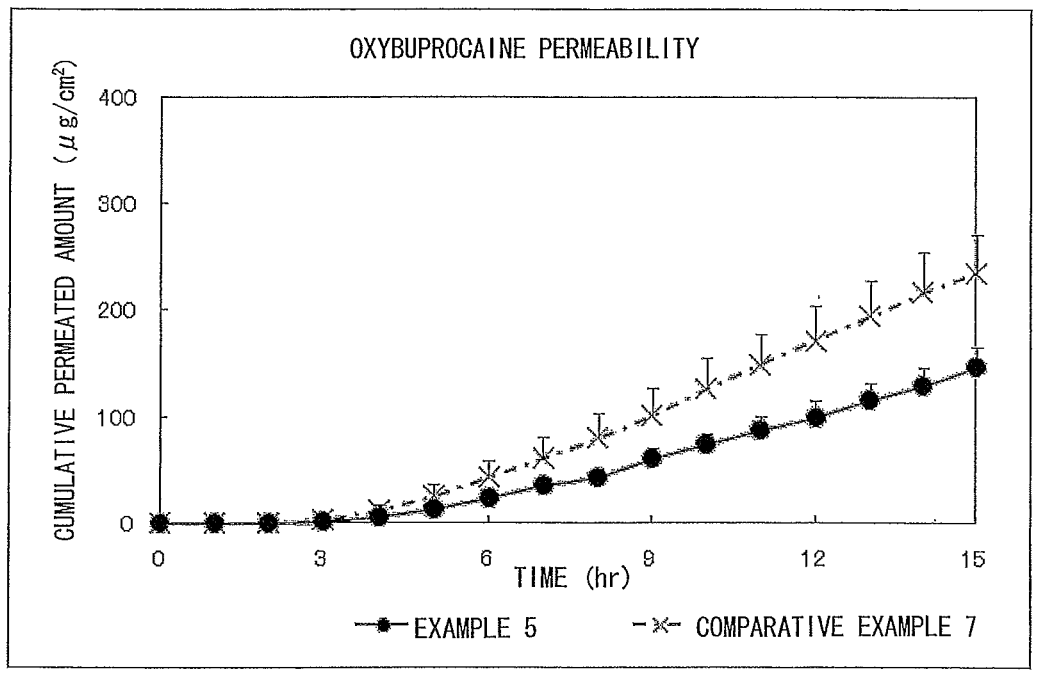
FIG. 10 is a graph showing the result of in vitro rat skin permeability test for oxybuprocaine based on Comparative Study (1)-5.
Figure 11:
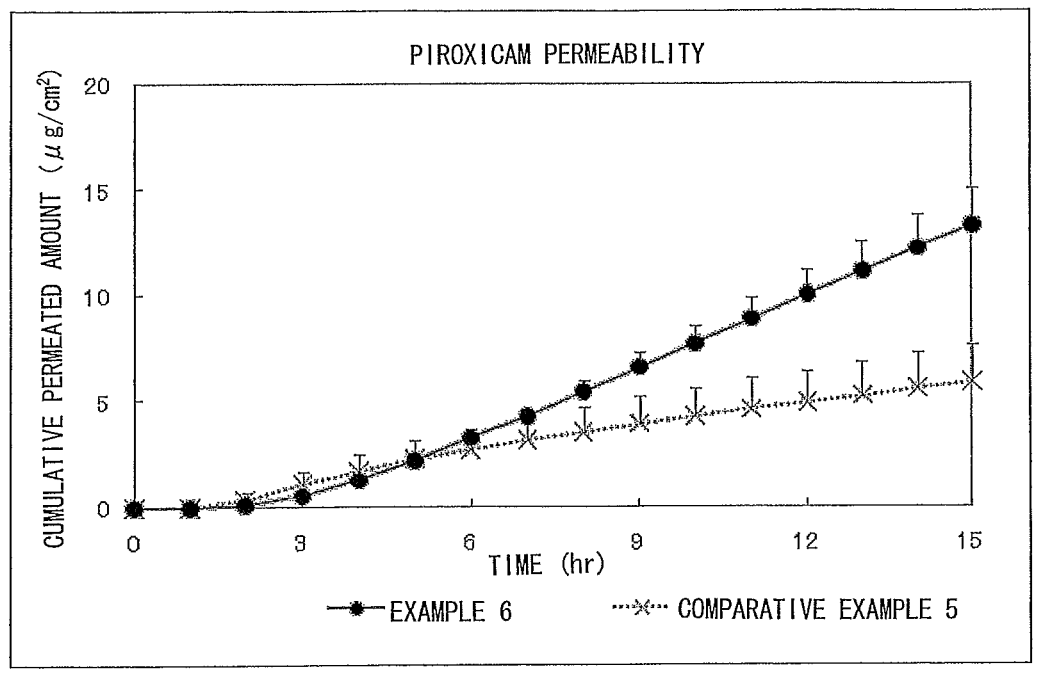
FIG. 11 is a graph showing the result of in vitro rat skin permeability test for piroxicam based on Comparative Study (1)-6.
Figure 12:
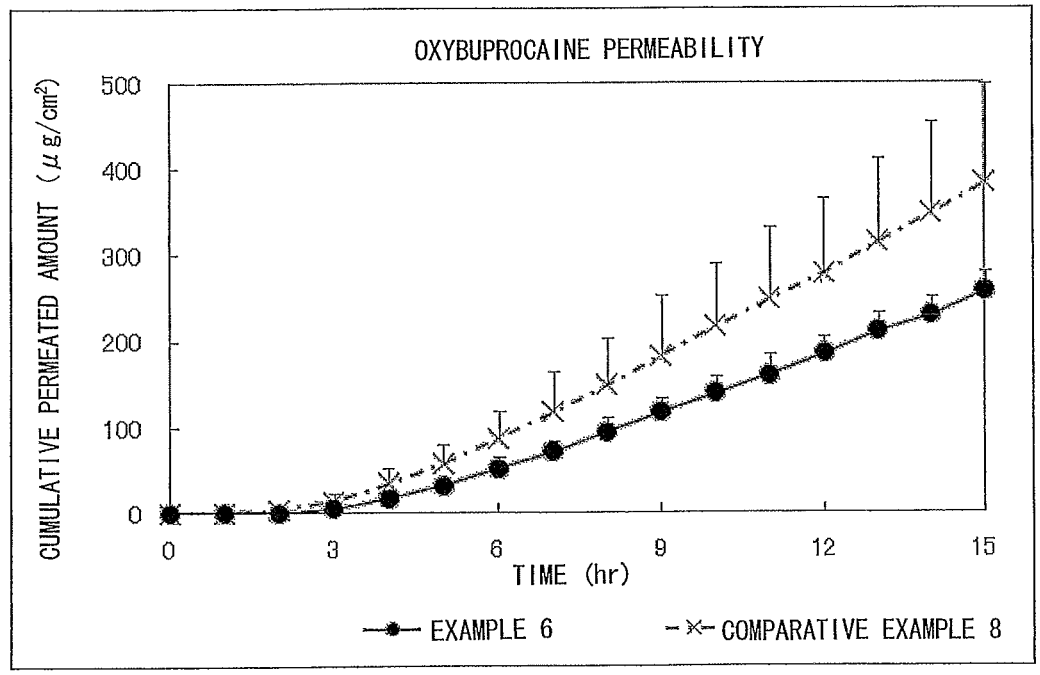
FIG. 12 is a graph showing the result of in vitro rat skin permeability test for oxybuprocaine based on Comparative Study (1)-6.

| Comparative Study Number | Result of Piroxicam Releasing Study | Result of Oxybuprocaine Releasing Study |
| --- | --- | --- |
| (1)-1 | FIG. 1 | FIG. 2 |
| (1)-2 | FIG. 3 | FIG. 4 |
| (1)-3 | FIG. 5 | FIG. 6 |
| (1)-4 | FIG. 7 | FIG. 8 |
| (1)-5 | FIG. 9 | FIG. 10 |
| (1)-6 | FIG. 11 | FIG. 12 |

Figure 13:
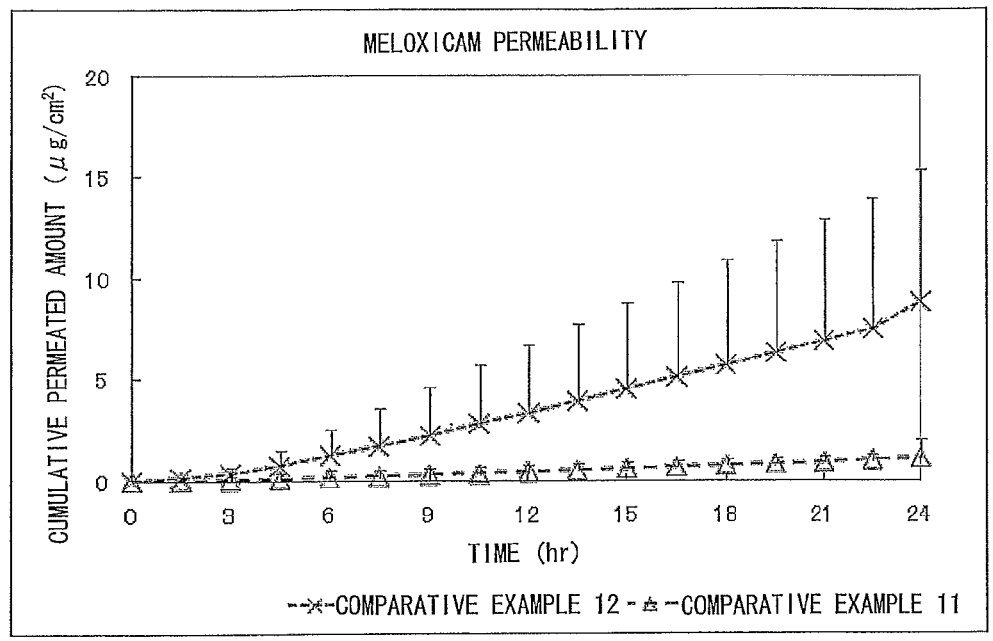
FIG. 13 is a graph showing the result of in vitro rat skin permeability test for meloxicam based on Comparative Study (2).
Figure 14:
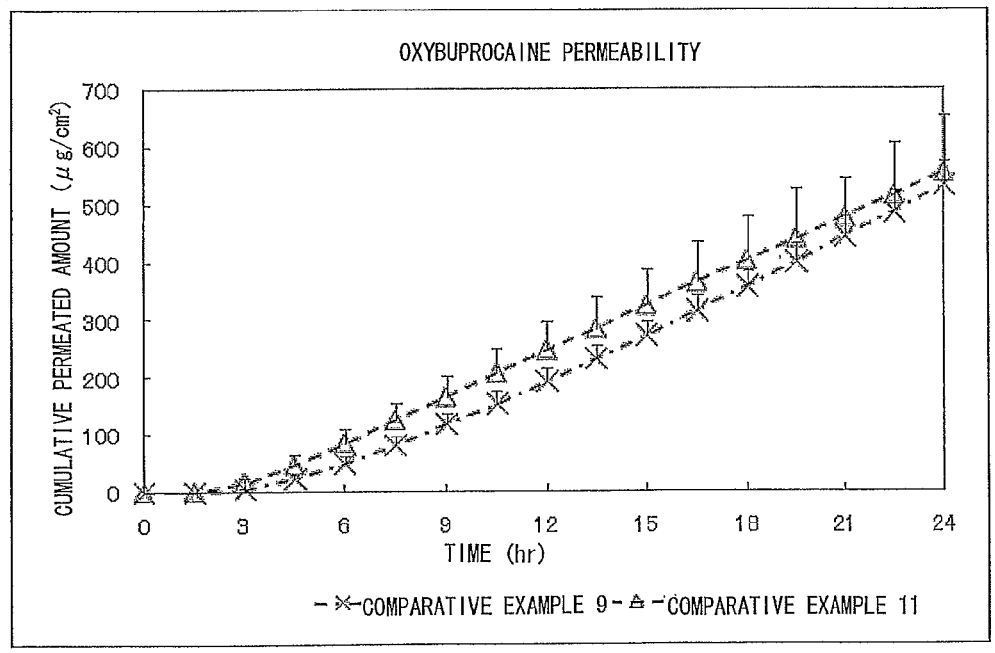
FIG. 14 is a graph showing the result of in vitro rat skin permeability test for oxybuprocaine based on Comparative Study (2).

| Comparative Study Number | Result of Meloxicam Releasing Study | Result of Oxybuprocaine Releasing Study |
| --- | --- | --- |
| (2) | FIG. 13 | FIG. 14 |

[Consideration]

Consideration to Comparative Study (1)

As is apparent in comparison of figures of correspondence relation shown in Table 4, the releasing of piroxicam in the external adhesive patch of the present invention in which both piroxicam and oxybuprocaine were formulated was dramatically high compared to the external adhesive patch of each Comparative Example in which only piroxicam was formulated. (FIG. 1, FIG. 3, FIG. 5, FIG. 7, FIG. 9 and FIG. 11).

Also, the releasing of oxybuprocaine in the external adhesive patch of the present invention was not inhibited significantly compared to the external adhesive patch of each Comparative Example in which only oxybuprocaine was formulated. In particular, in the external adhesive patch of Examples 1 to 3 in which the formulated ratio of piroxicam to oxybuprocaine was piroxicam:oxybuprocaine<1:15, the releasing of oxybuprocaine was almost the same as corresponding Comparative Examples in which only oxybuprocaine was formulated.

Considering these both results, it is understood that good releasing of oxybuprocaine as the absorption promoter enhances the releasing of piroxicam in the external adhesive patch of the present invention in which both piroxicam and oxybuprocaine are formulated.

Consideration to Comparative Study (2)

On the other hand, when meloxicam, which is another oxicam anti-inflammatory analgesic, was subjected to the same test, it was found that oxybuprocaine showed almost the same drug releasing regardless of whether meloxicam was formulated or not (FIG. 13), but the releasing of meloxicam was inhibited significantly by formulating oxybuprocaine (FIG. 14).

According to the results of these Comparative Studies (1) and (2), as for the adhesive patch of the present invention in which oxybuprocaine is formulated as the local anesthetic together with the piroxicam which is a non-steroidal anti-inflammatory analgesic, it was found that it is the transdermally absorbable preparation in which the releasing of oxybuprocaine is not inhibited significantly and accompanied by excellent piroxicam releasing although it is the preparation in which the basic drug of the local anesthetic and the acidic drug of the non-steroidal anti-inflammatory analgesic are formulated.

Further, the releasing effect of the anti-inflammatory analgesic, an active component, obtained by formulating oxybuprocaine is specific only for piroxicam among the oxicam anti-inflammatory analgesics. Therefore, it should be understood that the present invention has extremely excellent specificity.

Preparation Example

Hereinafter, specific Preparation Examples other than the external adhesive patch of the present invention described above in Example 1 are shown below in Table 5. Here, the present invention is not limited thereto.

TABLE 5

| Components | Preparation Example (unit: % by weight) | | | | | | |
| --- | --- | --- | --- | --- | --- | --- | --- |
| | 1 | 2 | 3 | 4 | 5 | 6 | 7 |
| SIS | 25 | 25 | 25 | 25 | 25 | 25 | 25 |
| BHT | 1 | 1 | 1 | 1 | 1 | 1 | 1 |
| Hydrogenated Rosin Glycerin Ester | 40 | 40 | 40 | | | | 42 |
| Terpene Resin | | | | | 40 | | 40 |
| Alicyclic Saturated Hydrocarbon Resin | | | | | | 40 | |
| Liquid Paraffin | 3 | 2 | 13.8 | 37.8 | 20.5 | 16 | 15.6 |

TABLE 5-continued

| | Preparation Example (unit: % by weight) | | | | | | |
|---|---|---|---|---|---|---|---|
| Components | 1 | 2 | 3 | 4 | 5 | 6 | 7 |
| Oxybuprocaine | 30 | 30 | 20 | 2 | 15 | 20 | 16 |
| Piroxicam | 1 | 2 | 0.2 | 0.2 | 1.5 | 1 | 0.4 |

The thickness of the adhesive layer: 100 μm

INDUSTRIAL APPLICABILITY

As described above, the transdermally absorbable preparation provided by the present invention can provide the preparation which shows excellent analgesic effect caused by oxybuprocaine and excellent anti-inflammatory effect caused by piroxicam.

In particular, in the present invention, by formulating specific amounts of piroxicam and oxybuprocaine as the absorption promoter to piroxicam in combination in the adhesive patch base, high releasing of piroxicam is kept without losing the releasing of oxybuprocaine significantly, thereby providing the transdermally absorbable preparation which achieves excellent anti-inflammatory and analgesic effects. Therefore, the present invention has a great medical effect.

The invention claimed is:

1. A transdermal adhesive patch comprising an adhesive patch base comprising a single non-steroidal anti-inflammatory analgesic (NSAID) and single absorption promoter of said NSAID, wherein the NSAID consists of piroxicam and the absorption promoter consists of oxybuprocaine or a pharmaceutically acceptable salt thereof, wherein the formulated ratio of piroxicam to oxybuprocaine or the pharmaceutically acceptable salt thereof is piroxicam:oxybuprocaine<1:2 by weight, wherein the piroxicam is present in an amount of 0.1% to 5% by weight of the total weight of said adhesive patch base and wherein the oxybuprocaine or the pharmaceutically acceptable salt thereof is present in an amount of 1% to 30% by weight of the total weight of said adhesive patch base.

2. The transdermal adhesive patch according to claim 1, wherein the formulated ratio of piroxicam to oxybuprocaine or the pharmaceutically acceptable salt thereof is piroxicam:oxybuprocaine<1:10 by weight.

3. The transdermal adhesive patch according to claim 1, wherein the adhesive patch base is a rubber polymer.

4. The transdermal adhesive patch according to claim 3, wherein the rubber polymer is a styrene-isoprene-styrene block copolymer.

5. The transdermal adhesive patch according to claim 2, wherein the adhesive patch base is a rubber polymer.

* * * * *